United States Patent [19]

Marschner

[11] 4,440,742
[45] Apr. 3, 1984

[54] BICARBONATE-CONTAINING STICK DEODORANT

[75] Inventor: Frank W. Marschner, Whitehouse Station, N.J.

[73] Assignee: Colgate-Palmolive Company, New York, N.Y.

[21] Appl. No.: 12,938

[22] Filed: Feb. 16, 1979

Related U.S. Application Data

[62] Division of Ser. No. 845,503, Oct. 25, 1977, abandoned.

[51] Int. Cl.³ ............................................. A61K 7/32
[52] U.S. Cl. ................................. 424/65; 424/DIG. 5; 424/346; 424/357; 424/362
[58] Field of Search ............................ 424/65, DIG. 5

[56] References Cited

U.S. PATENT DOCUMENTS

| | | | |
|---|---|---|---|
| 1,558,405 | 10/1925 | Smith | 424/65 |
| 2,857,315 | 10/1958 | Teller | 424/DIG. 5 |
| 2,900,306 | 8/1959 | Slater | 424/65 |
| 2,970,083 | 1/1961 | Bell | 424/68 |
| 3,090,728 | 5/1963 | Berger et al. | 424/DIG. 5 |
| 3,259,545 | 7/1966 | Teller | 424/DIG. 5 |
| 3,933,433 | 4/1960 | Teller et al. | 424/68 |

FOREIGN PATENT DOCUMENTS 760559 10/1956 United Kingdom ......... 424/DIG. 5

OTHER PUBLICATIONS

Janistyn, Riechstoffe Seifen Kosmetika, 1950, pp. 228 to 236, 409 & 410.
Goodman, Cosmetic Dermatology, pp. 363 to 367, 5/1937.

Primary Examiner—Dale R. Ore
Attorney, Agent, or Firm—Robert L. Stone; Murray M. Grill; Herbert S. Sylvester

[57] ABSTRACT

There is disclosed a stable cosmetic stick deodorant comprising a polyhydric alcohol solidified by a fatty acid soap and containing about 0.1 to 70% alkali metal bicarbonate without the use of bacteriostats, and the method of making said stick deodorants.

17 Claims, No Drawings

BICARBONATE-CONTAINING STICK DEODORANT

This is a divisional of application Ser. No. 845,503 filed Oct. 25, 1977, now abandoned.

This invention relates to a stable, saturated fatty acid soap based stick deodorant containing alkali metal bicarbonate as the essential deodorizing agent, and to the method of making said bicarbonate-containing deodorant sticks.

DESCRIPTION OF THE PRIOR ART

Cosmetic sticks having antiperspirant and/or deodorizing effects and based on alcoholic soap gels and/or propylene glycol soap gels are known in the prior art and are described in U.S. Pat. Nos. 2,900,306; 2,857,315; 2,933,433; 3,259,545; 2,970,083, Canadian Pat. No. 567,499 and British Pat. No. 795,773. The deodorizing agents heretofore incorporated into said soap gels include halogenated dihydroxy diphenyl methanes, particularly hexachlorophenes, as disclosed in U.S. Pat. Nos. 2,900,306 and 2,970,083.

In addition to or in lieu of aforesaid deodorants, antiperspirant agents such as sodium zirconium lactate, aluminum hydroxide gel, aluminum chlorhydroxy complex, aluminum hydroxy chloride, sodium aluminum chlorhydroxy lactate complex or mixtures thereof are added to said propylene glycol soap gel sticks as disclosed in U.S. Pat. Nos. 2,857,315; 2,933,433; 3,259,545; and 2,970,083.

Antiperspirants combat axillary odors by inhibiting perspiration through the action of astringent salts such as aluminum and zinc salts and may be irritating to a considerable number of users. On the other hand, deodorants neutralize the objectionable odors resulting from the degradation of the components of sweat due to chemical and microbial attack into foul smelling fatty acids. Deodorants do not inhibit sweating but rather neutralize the odorous degradation products of sweat, either by their own odorous properties, or by the inhibition of the decomposition action of microbial action on the fats in the sweat residues, or by reaction with the foul smelling fatty acids or by any combination of these mechanisms. Accordingly, they are not as irritating as the antiperspirants.

Sodium bicarbonate has long been recognized for its deodorant properties, and has commonly been used as a deodorant in refrigerators. In addition, plain powdered sodium bicarbonate or diluted with talc, cornstarch, rice-flour, or other filler has been used as an underarm deodorant as disclosed in the Journal of Investigative Dermatology Vol. 7, 1946 pages 131-133 and U.S. Pat. Nos. 279,195 and 1,558,405.

However, the development of a practical and effective deodorant composition in stick form, which is capable of consumer acceptability, presents many considerations which are unique. That is to say that, because sodium and potassium bicarbonate have only limited solubility in water, alcohol and other solvents, the preparation of a composition suitable for dispensing in stick form has been an exceedingly difficult and perplexing problem. In addition to the problem of limited solubility of the sodium bicarbonate, its compatibility with the other ingredients of conventional stick compositions, the dimensional stability of the stick containing sodium bicarbonate, its esthetic appearance and feel on the skin are just a few of the additional problems encountered in the preparation of an acceptable sodium bicarbonate-containing deodorant stick.

Accordingly, it is a primary object of this invention to provide a non-shrinking, non-stinging, stearate soap based deodorant stick containing an effective amount of an alkali metal bicarbonate as the active deodorant, the bicarbonate eliminating the need for bacteriostats as the deodorizing agent.

DESCRIPTION OF THE INVENTION

In accordance with the present invention, it has been found that a deodorant stick comprising at least 0.1 to 3% and preferably at least 1 to 3%, and up to 70%, and preferably up to 50% by weight of an alkali metal bicarbonate dispersed or dissolved in aqueous or anhydrous polyhydric alcohol per se, or in admixture with a monohydric alcohol, solidified by a minor amount of sodium stearate or a combination of sodium and potassium stearates, exhibits certain desirable characteristics.

More specifically, present invention relates to a deodorant cosmetic stick consisting essentially of at least about 0.1-3% and up to about 70% of an alkali metal bicarbonate, and about 0-10% suspending agent, dispersed in a soap based gel which comprises a major amount of an aqueous or anhydrous polyhydric alcohol or a mixture of a polyhydric and monohydric alcohol, gelled by a minor amount of an alkali metal salt of a fatty acid containing 14 to 20 carbon atoms.

The alkali metal bicarbonate incorporated into the fatty acid soap based stick will generally be sodium bicarbonate or potassium bicarbonate. It has been found that low levels of bicarbonate, up to about 3% can be readily dissolved in an aqueous solution in the preparation of a transparent stick. Higher levels of about 8% potassium bicarbonate can also be used in the preparation of solid deodorant sticks. However, larger amounts of sodium or potassium bicarbonate, beyond their solubility range can also be incorporated into said sticks by using a suspending agent and micro-pulverized sodium or potassium bicarbonate powder, having a particle size of about 5 to 100 microns and preferably 10 to 25 microns. The smaller the particles, the easier it is to suspend in the soap gel; and the resultant stick affords a non-gritty, smoother feel upon application to the skin.

Accordingly, extra strength deodorant sticks, i.e., containing more than 3% bicarbonate, can also be formulated by adding a suitable suspending agent, which are known bulking agent compounds such as colloidal silica such as "Cab-O-sil"; a pyrogenic silica having a particle diameter between about 0.001 and 0.03 microns as disclosed in British Pat. No. 987,301; colloidal (fumed) alumina; finely divided hydrophobically treated clays such as a reaction product of a clay such as bentonite or hectorite with, for example, dimethyldistearyl ammonium chloride; colloidal magnesium aluminum silicates; other montmorillonite clays; and hydrophobically treated montmorillonite clays. All patents referred to in this application are specifically incorporated herein by reference.

The preferred suspending agents are the hydrophobically treated montmorillonite or hectorite clays available under the trademark "Bentone" which are prepared by reacting a clay such as bentonite or hectorite in a cation exchange system with a variety of amines. Different amines are reacted to obtain differenet Bentone suspending agents which may also differein proportions of $SiO_2$, $MgO$ and $Al_2O_3$, all of which have a particle size below about 5 microns and are commercially available from the NL Industries, Inc. The suspending agent is employed in amounts of about 0.1 to 10% and preferably 0.5 to 2% by weight of the total composition.

The transparency of the bicarbonate stick is reduced as the solubility of the bicarbonate in the soap gel is reduced, because part of the bicarbonate is now in suspension, resulting in an opaque stick. These opaque sticks which contain up to 70% and preferably up to 50% bicarbonate are very effective stick deodorants and feel like a cream when applied to the skin, without affecting the hardness characteristics of the stick. Partial substitution of talc for bicarbonate gives added improvement to the after feel of such sticks.

It has additionally been found that the substitution of water-absorptive insoluble filler materials in finely divided particulate form such as talc, cornstarch and the like for a portion of the bicarbonate content, not to exceed the amount of bicarbonate, can also be incorporated into the soap based gel stick to give a smooth feel and/or water absorbing properties to the product. Such materials act by absorbing sweat under the armpit assuring a dry feeling without altering the normal perspiration process.

It has also been found that sodium or potassium bicarbonate buffers and lowers the pH of the soap based stick deodorant from about 10 to about 8.5 to 9, and from 10.5 to 9.5 respectively, thereby reducing possible skin sensitivity without adversely affecting the required hardness characteristics of the stick.

The sodium or potassium soap based gel into which the aqueous bicarbonate solution or suspension is incorporated comprises a polyhydric alcohol or a mixture of a polyhydric and monohydric alcohol, a solidified or gelled by means of an alkali metal salt of a saturated fatty acid containing about 14 to 20 carbon atoms. Suitable polyhydric alcohols include glycerin and the lower alkylene glycols of low molecular weight which are liquid at room temperature, such as ethylene glycol, diethylene glycol, butylene glycol and preferably propylene glycol. The alcohol content which includes the polyhydric alcohol and monohydric alcohol (if any) constitutes the major liquid ingredient of instant composition, from about 20% to 90% by weight of the total composition.

The monohydric alcohol which is a lower alkanol such as ethanol or isopropyl alcohol may be substituted for only part of the polyhydric alcohol, not to exceed 2.5 times that of the polyhydric alcohol and preferably not to exceed the polyhydric alcohol content. These combined alcohol containing sticks are also effective as deodorant sticks. However, transparency of the alcohol containing stick is reduced considerably, i.e., said sticks are opaque, not transparent or translucent. The use of ethanol as the sole alcohol base has been found to be undesirable due to its drying out properties, i.e., syneresis.

The polyhydric alcohol or the combination of ethanol with the polyhydric alcohol, specifically propylene glycol is converted into a gel with a solidifying ingredient in a known manner to form the solid cosmetic product. In particular, it is preferred to employ a stearic acid soap as the gelling agent which is formed preferably in situ by the admixture of aqueous alkali such as sodium or potassium hydroxide with a warm solution of stearic acid in propylene glycol or mixture thereof with ethanol. The resulting mixture solidifies to a gel upon cooling. Any type of high molecular weight saturated fatty acid may be used though it is preferred to employ the commercial stearic acid which comprises essentially a mixture of stearic and palmitic acids. The solidifying agent is used in minor amounts of about 2 to 15% and preferably about 4–8% by weight. Although a sodium, potassium, or sodium-potassium stearate is contemplated as the gelling agent, the sodium stearate is preferred.

In addition to the essential components of the present composition, one may also include therein minor amounts of components such as perfumes, coloring agents, ultraviolet absorbers to enhance the color, and the like, so as to improve the aesthetic value and consumer acceptability.

Other optional ingredients in minor amounts may be incorporated in instant composition without adversely affecting the beneficial properties thereof such as the potassium, aluminum and amine soaps, emollients and emulsifiers such as silicones, fatty esters, fatty amides, fatty alcohols, ethoxylated fatty alcohols and acids. These emulsifiers help make the sticks into a melting stick so that upon contact with the skin, a layer of the composition is deposited thereon. Preferred emulsifiers include alkoxylated cetyl alcohol such as polypropylene glycol of the condensate of cetyl alcohol with 20 moles of ethylene oxide, oleyl alcohol, ethoxylated lanolin, particularly Solulan which is a polyethylene glycol ether of lanolin alcohols (average 16 moles ethylene oxide).

Another optional ingredient having beneficial affects on the present deodorant stick are thickeners or viscosity builders which alone or in combination with suspending agents retard the settling out of materials before the gel solidifies. Particularly useful thickeners include cellulosic derivatives such as hydroxyethyl cellulose, hydroxypropyl cellulose, sodium carboxymethyl cellulose (CMC) and Methacel which is a hydroxypropylmethyl cellulose containing about 23–32% hydroxypropyl groups, about 16.5–20% methyl groups and about 5% NaCl, having a viscosity of about 4000–6000 centipoises.

Known bacteriostats may also be added, although the bicarbonate-containing stick per se is effective as a deodorant without the use of added bacteriostats.

The method of making the aqueous bicarbonate-containing deodorant stick of instant invention generally comprises mixing an aqueous dispersion or solution of the bicarbonate plus suspending agent (when used) with a hot or heated solution of polyhydric alcohol, stearic acid and alkali metal hydroxide, preferably at about 160° F.; followed by the addition of perfume, colorants and other optional ingredients, (if any) to form a homogeneous liquid product; pouring the warm liquid into molds and cooling to room temperature. During the cooling period, gelation takes place and the resultant product assumes a rigid form which is capable of application to the skin by gently rubbing, whereby a thin film of said composition is deposited on the desired areas of the skin. The resultant rigid stick is transparent or opaque, depending on the amount of bicarbonate added and the particular ingredient employed. This stick is stable, i.e., there is no separation out of specific ingredients; and it possesses a good shelf-life, i.e., no syneresis or shrinkage occurs.

Another method of making the aqueous bicarbonate-containing sticks of instant invention comprises the addition of the powdered bicarbonate and filler such as talc (if desired) directly to the hot liquid soap base with agitation, and pouring the warm flowable mixture into containers to harden into deodorant sticks.

A preferred method of making said bicarbonate-containing stick is to combine the stearic acid with sodium carbonate or potassium carbonate to form the sodium or potassium soap and the sodium or potassium bicarbonate in situ. This reaction is shown by the following equation wherein R represents the stearyl radical:

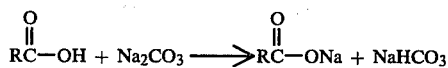

The method of preparing the anhydrous soap based sticks comprises dissolving the alkali metal soap such as the stearate in hot polyhydric alcohol containing a suspending agent; adding the bicarbonate thereto with agitation; followed by the addition of the water absorptive materials, perfume, coloring agents, etc.; and pouring the resultant mixture into containers to cool and solidify.

The following specific examples are further illustrative of the present invention, but it is understood that the invention is not limited thereto. All amounts of various ingredients are by weight unless otherwise specified.

EXAMPLES 1-5

(Na Soap—Propylene Glycol—Water Based)

| Example | 1 | 2 | 3 | 4 | 5 |
|---|---|---|---|---|---|
| Part 1 | | | | | |
| Propylene Glycol | 53.45 | 53.35 | 52.45 | 50.45 | 45.45 |
| Stearic Acid | 6.00 | 6.00 | 6.00 | 6.00 | 6.00 |
| 19.1% $Na_2O$ Caustic Soda | 3.60 | 3.60 | 3.60 | 3.60 | 3.60 |
| Part 2 | | | | | |
| Deionized water | 35.6 | 35.6 | 35.6 | 35.6 | 28.20 |
| Sodium Bicarbonate | — | 0.1 | 1.0 | 3.0 | — |
| Sodium Bicarbonate (Micro pulverized) | — | — | — | — | 15.00 |
| Bentone LT | — | — | — | — | 0.50 |
| Part 3 | | | | | |
| Perfume | 1.00 | 1.00 | 1.00 | 1.00 | 1.00 |
| Triclosan (Bacteriostat)[1] | 0.10 | 0.10 | 0.10 | 0.10 | — |
| Uvinul 400 (Ultraviolet absorber)[2] | 0.05 | 0.05 | 0.05 | 0.05 | 0.05 |
| Part 4 | | | | | |
| FDC Blue #1 0.1% of Soln. | 0.20 | 0.20 | 0.20 | 0.20 | 0.20 |
| | 100.00 | 100.00 | 100.00 | 100.00 | 100.00 |
| Visual Appearance | Translucent to Opaque | Transparent | Transparent | Translucent | Opaque |
| pH (10% Aqueous Soln.) | 10.32 | 9.7 | 9.1 | 8.9 | 8.5 |

[1]4,2',4'trichloro-2-hydroxy diphenyl ether
[2]2,4 dihydroxy benzophenone

The stearic acid and the propylene glycol are mixed and heated to 160° F., followed by addition of the caustic soda.

The Bentone is gradually added to the water with rapid and/or high shear mixing, followed by the addition of the sodium bicarbonate.

The two solutions are mixed together and cooled to 125°-130° F. The perfume, bacteriostat and uvinol are admixed and added to the above mixture, followed by the addition of the coloring agent.

The total mixture is poured into molds and chilled to solidify into stable deodorant sticks.

These examples clearly show the buffering affect of the sodium bicarbonate, as well as the improved transparency of the stick at concentrations of 0.1 to 3% bicarbonate content.

The pH measurements are made by dissolving 10 gms of stick deodorant in 90 gms deionized water by heating, and then cooling to room temperature before taking readings.

EXAMPLES 6 & 7

(Na Soap—Propylene Glycol—Ethanol—Water Based)

| Example | 6 | 7 |
|---|---|---|
| Part 1 | | |
| Propylene Glycol | 32.80 | 32.80 |
| Ethanol (95%) | 35.75 | 32.75 |
| Stearic Acid (B Grade) | 6.00 | 6.00 |
| 19.1% $Na_2O$ Caustic Soda | 3.60 | 3.60 |
| Part 2 | | |
| Deionized Water | 20.00 | 20.00 |
| Sodium Bicarbonate | — | 3.00 |
| Part 3 | | |
| Perfume | 1.00 | 1.00 |
| Triclosan (Bacteriostat) | 0.10 | 0.10 |
| Uvinul 400 | 0.05 | 0.05 |
| Butyl Stearate | 0.50 | 0.50 |
| Part 4 | | |
| FDC Blue #1 0.1% aq. soln | 0.20 | 0.20 |
| | 100.00 | 100.00 |
| Visual Appearance | Opaque | Opaque |
| pH | 9.5 | 8.8 |

The same procedure as in Example 1-5 is followed.

These examples also show the buffering action of the bicarbonate in the presence of a mixture of ethanol and propylene glycol.

EXAMPLES 8 & 9

(Combining Stearic Acid with Sodium Carbonate)

| Example | 8 | 9 |
|---|---|---|
| Part 1 | | |
| Propylene Glycol | 53.45 | 52.60 |
| Stearic Acid (B Grade) | 6.00 | 6.00 |
| Trichlorocarbanilide (TCC) | 0.15 | — |
| Part 2 | | |
| Deionized water | 36.6 | 33.75 |
| Sodium Carbonate | 2.4 | 2.40 |
| Sodium Bicarbonate | — | 3.00 |
| Bentone LT | — | 0.50 |
| Methocel (thickener)[1] | — | 0.40 |
| Part 3 | | |
| Perfume | 1.00 | 1.00 |
| Uvinul 400 | 0.05 | 0.05 |
| Triclosan (Bacteriostat) | 0.05 | — |
| Part 4 | | |
| FDC Blue #1 0.1% aq. Soln | 0.30 | 0.30 |
| | 100.00 | 100.00 |
| Visual Appearance | Transparent | Opaque |
| pH (10% aqueous Soln) | 9.0 | 8.8 |

[1]hydroxy propylmethyl cellulose

Part 1 is prepared by heating and dissolving the TCC and the stearic acid in propylene glycol at 160° F.

Part 2 is prepared by dissolving the sodium carbonate and/or the sodium bicarbonate in water with mixing and heating to 160° F. Methocel is gradually added with rapid mixing followed by the gradual addition of Bentone.

Part 1 is gradually added to Part 2 and cooled to about 130° F.

Part 3 ingredients are admixed and added to the above liquid mixture, followed by the addition of the color. This homogeneous mixture is poured into molds and chilled.

These examples are specific to the preferred method of forming the sodium bicarbonate in situ by the addition of stearic acid to the sodium carbonate. The stick containing less than 3% bicarbonate is transparent, whereas the greater quantity of bicarbonate produces an opaque stick.

In example 9, the total quantity of sodium bicarbonate formed exceeds its solubility in the system so that the excess amount precipitates out as fine particles on the Bentone suspending agent.

EXAMPLES 10-12

| Example | 10 | 11 | 12 |
|---|---|---|---|
| Propylene glycol | 53.45 | 53.45 | 53.45 |
| Stearic Acid | 6.00 | 6.00 | 6.00 |
| TCC | 0.15 | 0.15 | 0.15 |
| Deionized Water | 33.5 | 33.4 | 33.4 |
| Caustic Soda (19.1%) | 3.6 | 3.6 | 3.6 |
| NaCl | — | 0.1 | — |
| Sodium Bicarbonate | — | — | 0.1 |
| Diisopropyl adipate | 1.0 | 1.0 | 1.0 |
| Benzyl alcohol | 1.0 | 1.0 | 1.0 |
| Lavender | 1.0 | 1.0 | 1.0 |
| FDC Blue #1 (0.1%) | 0.2 | 0.3 | 0.3 |
| U.V. 400 | 0.05 | 0.05 | 0.05 |
| DP 300 | 0.05 | 0.05 | 0.05 |

Example 12 is significantly more transparent than Examples 10 and 11 and retains its transparency after 20 minutes at 0° in a freezer, whereas the other sticks become slightly hazy after freezing, thereby demonstrating the superior stability of the bicarbonate-containing stick. In addition, Example 12 retains its transparency after standing overnight, whereas the other sticks become less transparent.

EXAMPLES 13 & 14

Cream Sticks

| Example | 13 | 14 |
|---|---|---|
| Base | A | C |
| Part 1 | | |
| Propylene Glycol | 55.0 | 75.73 |
| Stearic Acid (Double pressed grade) | 6.0 | — |
| Stearic Acid (Triple Pressed grade) | — | 5.00 |
| Bentone LT | 2.0 | 1.00 |
| Tallow Fatty Acid | — | 1.00 |
| Part 2 | | |
| Water | 26.48 | 10.0 |
| Soda Ash (Sodium Carbonate) | 2.40 | 2.37 |
| Part 3 | | |
| Perfume | 1.0 | 1.0 |
| Glycerol Monostearate | — | 0.5 |
| Procetyl AWS (emulsifier)[1] | 7.0 | 3.0 |
| D & C Green 8 (2.75%) | 0.08 | — |
| FDC Green 3 (0.1%) | 0.04 | — |
| D & C Red 19 (0.1%) | — | 0.4 |
| | 100.00 | 100.00 |
| | 50% Cream Stick | 50% Cream Stick |

-continued

| Example | 13 | 14 |
|---|---|---|
| Base | A | C |
| | Base A | Base C |
| | 50% Baking Soda (Micropulverized) | 25% Baking Soda (Micropulverized) |
| | | 25% Italian Talc |
| | 100% | 100% |

Part 1 ingredients are admixed and heated to 160° F. and added to the aqueous solution of Part 2 at 160° F. The mixture is cooled to 140° F. and a mixture of Part 3 ingredients are added thereto with mixing to form the cream stick base.

The micropulverized baking soda per se or jointly with the talc powder are mixed with the hot liquid cream base at a temperature of at least 125° F. The warm flowable mixture is poured into containers and cooled to form a solid stick. These high solid stick deodorants go on the skin like a cream. The talc baking soda sticks give a particularly smooth feel when rubbed on the skin.

EXAMPLES 15 & 16

(Use of Potassium Bicarbonate)

| Example | 15 | 16 |
|---|---|---|
| Part 1 | | |
| Propylene Glycol | 52.3 | 44.3 |
| Sodium Stearate | 8.0 | 8.0 |
| Procetyl AWS | 3.0 | 3.0 |
| Part 2 | | |
| Deionized water | 35.0 | 35.0 |
| Potassium Bicarbonate | 0 | 8.0 |
| Part 3 | | |
| Sodium Chloride | 0.2 | 0.2 |
| Perfume | 1.5 | 1.5 |
| | 100.00 | 100.00 |
| Appearance | Translucent to Transparent | Translucent to Transparent |
| pH (10% aqueous solution) | 10.5 | 9.5 |

Sodium stearate and procetyl AWS are dissolved in hot propylene glycol at about 180° F. Potassium bicarbonate is dissolved in warm deionized water. Part 2 is added to Part 1 with mixing and Part 3 ingredients are admixed.

Results show the buffering affect of potassium bicarbonate and its usefulness at 8% in solution.

EXAMPLE 17

| Example | 17 |
|---|---|
| (Anhydrous Stick) | |
| Propylene Glycol | 75.8 |
| Sodium Stearate | 8 |
| Procetyl AWS | 4 |
| Sodium Bicarbonate (micropulverized) | 10 |
| Bentone LT | 0.5 |
| Perfume | 1.5 |
| FDC Green #3 (0.1% in ethanol) | 0.2 |
| | 100.00 |
| Appearance | Greenish opaque (with good aesthetics) |

Bentone LT is dispersed in propylene glycol and procetyl AWS solution with rapid mixture. Sodium stearate is dissolved in the mixture at about 185° F. The temperature is reduced to 160° F. and the sodium bicarbonate powder is admixed followed by perfume and color. The product is poured into containers and cooled to form a solid stick.

EXAMPLE 18

| Example | 18 |
|---|---|
| (Substitution of Glycerine for Propylene Glycol) | |
| Part 1 | |
| Glycerine | 50.00 |
| Stearic Acid (Double Pressed Grade) | 6.00 |
| Part 2 | |
| Deionized water | 35.83 |
| Soda Ash (Sodium Carbonate | 2.40 |
| Part 3 | |
| Perfume | 1.50 |
| Triclosan (Bacteriostat) | 0.15 |
| Procetyl AWS | 4.00 |
| D & C Green #8 (2.75%) | 0.08 |
| FDC Green #3 (0.1%) | 0.04 |
| | 100.00 |
| Appearance | Transparent |

Part 1 is prepared by dissolving stearic acid in glycerine at 160° F.

Part 2 is prepared by dissolving soda ash in deionized water at 160° F.

Part 1 is added gradually to Part 2 with mixing and cooled to 145° F.

Part 3 ingredients are admixed and the solution is poured into containers and cooled to form a solid stick.

Other polyhydric alcohols can be substituted for propylene glycol in part or in total in the above Examples, such as ethylene glycol, butylene glycol, etc. Similarly the ethanol can be replaced by other monohydric alcohols such as isopropyl alcohol. Likewise, other fatty acid soaps can be substituted for the stearate soap.

All of the sticks containing the bicarbonate have been found to be a highly effective deodorant without the use of bacteriostats, stable, non-stinging and non-shrinking.

Although the present invention has been described and illustrated with reference to specific examples, it is understood that modifications and variations of composition and procedure are contemplated within the scope of the following claims.

I claim:

1. A stable transparent water-based deodorant stick comprising a water-soluble amount of at least 0.1% by weight of sodium or potassium bicarbonate as the essential deodorizing agent, dissolved in an aqueous polyhydric alcohol, solidified by an alkali metal salt of a saturated $C_{14}$–$C_{20}$ fatty acid gelling agent, said polyhydric alcohol constituting about 20–90% by weight of the total composition.

2. A deodorant stick in accordance with claim 1, wherein the alkali metal bicarbonate is formed in situ simultaneously with the alkali metal stearate soap by reacting the stearic acid with alkali metal carbonate.

3. A deodorant stick in accordance with claim 1, wherein the polyhydric alcohol is selected from the group consisting of glycerine and lower alkylene glycols of low molecular weight which are liquid at room temperature.

4. An opaque deodorant stick in accordance with claim 3, wherein a monohydric alcohol is substituted for about one half the polyhydric alcohol content.

5. A deodorant stick in accordance with claim 1, wherein the gelling agent is sodium stearate and constitutes about 2–15% by weight.

6. A deodorant stick in accordance with claim 4, wherein the polyhydric alcohol is propylene glycol and the monohydric alcohol is ethanol.

7. A transparent deodorant stick in accordance with claim 3, containing about 0.1–3% sodium bicarbonate.

8. A transparent deodorant stick in accordance with claim 3, containing about 0.1–8% potassium bicarbonate.

9. An opaque deodorant stick in accordance with claim 4, containing about 0.1–3% sodium bicarbonate.

10. An opaque deodorant stick in accordance with claim 4, containing about 0.1–8% potassium bicarbonate.

11. A transparent deodorant stick in accordance with claim 3, wherein the polyhydric alcohol is propylene glycol and the gelling agent constitutes about 2–15% by weight of the total composition.

12. A deodorant stick in accordance with claim 1, obtained by reacting an aqueous sodium or potassium carbonate solution with an alcoholic fatty acid solution, whereby the bicarbonate is formed in situ simultaneously with the sodium or potassium fatty acid gelling agent.

13. A method of preparing a stable water-based deodorant stick containing a water-soluble amount of sodium or potassium bicarbonate, which comprises mixing an aqueous solution of said bicarbonate with a heated solution comprising about 20–90% by weight polyhydric alcohol, and an alkali metal salt of a saturated $C_{14}$–$C_{20}$ fatty acid gelling agent, to form a warm homogeneous liquid product, pouring the warm liquid into molds and cooling to room temperature to solidify said liquid into a rigid transparent deodorant stick.

14. A method in accordance with claim 13, wherein said gelling agent is formed in situ by the reaction of a $C_{14}$–$C_{20}$ saturated fatty acid with an alkali metal hydroxide, dissolved in said heated polyhydric alcohol.

15. A method in accordance with claim 14, wherein the polyhydric alcohol is propylene glycol and the fatty acid is stearic acid.

16. A method in accordance with claim 13, wherein a lower alkanol is added to the heated solution in an amount not to exceed the polyhydric content, and recovering an opaque deodorant stick.

17. A method in accordance with claim 13, wherein both the bicarbonate and the alkali metal fatty acid gelling agent are simultaneously formed in situ by the reaction of an aqueous solution of sodium or potassium carbonate with a heated polyhydric alcohol solution of a $C_{14}$–$C_{20}$ saturated fatty acid.

* * * * *